United States Patent
Earl et al.

(10) Patent No.: US 7,333,591 B2
(45) Date of Patent: *Feb. 19, 2008

(54) METHOD FOR THE PLANNING AND DELIVERY OF RADIATION THERAPY

(75) Inventors: Matt A. Earl, Columbia, MD (US); David M. Shepard, Severn, MD (US); Xinsheng Yu, Clarksville, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/588,294

(22) Filed: Oct. 27, 2006

(65) Prior Publication Data

US 2007/0064871 A1 Mar. 22, 2007

Related U.S. Application Data

(63) Continuation of application No. 10/308,090, filed on Dec. 3, 2002, now Pat. No. 7,162,008.

(60) Provisional application No. 60/338,118, filed on Dec. 3, 2001.

(51) Int. Cl.
*A61N 5/10* (2006.01)
(52) U.S. Cl. .......................... 378/65; 378/149; 378/151; 378/152
(58) Field of Classification Search .................. 378/64, 378/65, 147–153
See application file for complete search history.

(56) References Cited

U.S. PATENT DOCUMENTS

| 5,596,619 | A | 1/1997 | Carol |
| 5,802,136 | A | 9/1998 | Carol |
| 6,038,283 | A | 3/2000 | Carol et al. |
| 6,128,366 | A | 10/2000 | Siochi |
| 6,219,403 | B1 | 4/2001 | Nishihara |
| 6,240,161 | B1 | 5/2001 | Siochi |
| 6,240,162 | B1 | 5/2001 | Hernandez-Guerra et al. |
| 6,260,005 | B1 | 7/2001 | Yang et al. |
| 6,504,899 | B2 | 1/2003 | Pugachev et al. |
| 6,907,105 | B2 | 6/2005 | Otto |
| 7,162,008 | B2 * | 1/2007 | Earl et al. ............... 378/65 |

OTHER PUBLICATIONS

Convery et al., "The generation of intensity-modulated fields for conformal radiotherapy by dynamic collimation," *Phys. Med. Biol.*, (1992), vol. 37, No. 6, pp. 1359-1374.
Yu et al., "A method for implementing dynamic photon beam intensity modulation using independent jaws and a multileaf collimator," *Phys. Med. Biol.*, (1995), vol. 40, pp. 769-787.
Boyer et al., "Intensity-Modulated Radiation Therapy With Dynamic Multileaf Collimators," *Seminars in Radiation Oncology*, vol. 9, No. 1, (Jan. 1999), pp. 48-59.
Bortfeld et al., "X-Ray Field Compensation with Multileaf Collimators," *Int. J. Radiation Oncology Biol. Phys.*, vol. 28, No. 3, (1994), pp. 723-730.
Yu et al., "Clinical Implementation of Intensity-Modulated Arc Therapy," *Int. J. Radiation Oncology Biol. Phys.*, vol. 53, No. 2 (2002), pp. 453-463.
Webb, "The Physics of Three-Dimensional Radiation Therapy—Conformal Radiotherapy, Radiosurgery and Treatment Planning," *IOP Publishing, Inc.*, (1993), Philadelphia, PA.
Webb, "Levitt and Tapley's Technological Basis of Radiation Therapy : Practical Clinical Applications," *Lea & Febiger*(1992), Malvern, PA.
Yu, "Intensity-modulated arc therapy with dynamic multileaf collimation: an alternative to tomotherapy," *Phys. Med. Biol.*, (1995), vol. 40, pp. 1435-1449.

* cited by examiner

*Primary Examiner*—Jurie Yun
(74) *Attorney, Agent, or Firm*—Sughrue Mion, Pllc.

(57) ABSTRACT

A new optimization method for generating treatment plans for radiation oncology is described and claimed. This new method works for intensity modulated radiation therapy (IMRT), intensity modulated arc therapy (IMAT), and hybrid IMRT.

4 Claims, 3 Drawing Sheets

METHOD FOR THE PLANNING AND DELIVERY OF RADIATION THERAPY

BACKGROUND OF THE INVENTION

This is a continuation of Application Ser. No. 10/308,090 filed Dec. 3, 2002 now U.S. Pat. No. 7,162,008, which claims benefit of Provisional Application No. 60/338,118 filed Dec. 3, 2001. The entire disclosure of the prior application, application number 10/308,090 is hereby incorporated by reference.

This invention was made with the support of the U.S. government under Grant Number R29CA66075 awarded by NIH. The U.S. government has certain rights in this invention.

SUMMARY OF THE INVENTION

A computer listing of a program according to an exemplary embodiment of the invention is submitted herewith in a CD-ROM as an Appendix to this application. The contents of the CD-ROM are incorporated by reference. The computer program is subject to copyright protection.

1. Field of the Invention

The present invention relates to a computerized method for the planning and delivery of radiation therapy. In particular, it is a computerized method that determines the optimal radiation treatment plan for a patient using specified clinical objectives.

2. Description of Related Art

Radiation therapy, in general, is the use of ionizing radiation for the treatment of disease. The most common use is in the treatment of cancer. The goal of radiation therapy for cancer is to destroy any diseased cells while minimizing the damage to healthy tissue. One device for delivering the radiation to a patient is with a linear accelerator, a machine that generates a high-energy beam of radiation that can be controlled and directed onto specified locations. Linear accelerators are sometimes equipped with a multi-leaf collimator (MLC), a device that shapes each individual beam of radiation.

Prior art treatment planning for conventional cancer radiation treatment is often performed with the aid of three-dimensional patient images acquired using a computed tomography (CT) scanner. Using the three-dimensional patient images, the radiation oncologist pinpoints the location of the tumor and any surrounding sensitive structures. Using the information provided by the radiation oncologist, a treatment planner devises the configuration of radiation beams that will deliver the desired radiation dose to the patient. The parameters that need to be determined by the treatment planner include the beam energies, beam orientations, and field shapes. (Levitt et. al., "Technological Basis for Radiation Therapy: Clinical Applications", 3rd Ed., Lippincott, William & Wilkins (1999)) Using a trial-and-error approach, the treatment planner determines an acceptable configuration of the various parameters that meets the clinical goals specified by the radiation oncologist. This approach is called "forward-planning" because a human being determines the parameters that produce the best treatment plan. (Levitt, et. al.)

Prior art treatment planning uses a "forward-planning" technique for conventional cancer radiation treatment by shaping the radiation field. However, shaping the radiation field alone restricts one's ability to shape the volume of the high radiation dose to conform to the tumor. As a result, adverse complications can arise in the patient being treated because of irradiation of normal structures.

A recent development in radiation therapy is intensity-modulated radiotherapy (IMRT) in which the intensity of the radiation delivered is modulated within each field delivered. (Webb, "The Physics of Conformal Radiotherapy", Institute of Physics Publishing, Bristol (1997)) The purpose of IMRT is to sculpt the radiation dose distribution so that it maximizes the radiation dose to the tumor while maintaining the radiation dose to normal structures within some pre-specified tolerance. (Webb) In IMRT, highly conformal dose distributions can be achieved through the delivery of optimized non-uniform radiation beam intensities from each beam angle. Successful delivery of IMRT can allow for an escalation of the tumor dose and may enhance local tumor control. The dosimetric advantages of IMRT can also be used to provide a reduced probability of normal tissue complications.

Because of the complexity of the treatment plans for IMRT, an automated system is required to determine the intensity maps that produce the optimal radiation dose distribution. In contrast to prior art "forward planning" techniques, this approach is termed "inverse-planning" because the automated system detetinines the parameters that produce the optimal radiation treatment plan. (Webb)

Currently available IMRT delivery techniques include fixed field beam delivery (IMRT) and intensity modulated arc therapy (IMAT). When radiation is delivered with fixed beam angles, a series of beam shapes are delivered at each beam angle either dynamically, where the leaves of the MLC move during irradiation, or in a step-and-shoot fashion, where the radiation is paused during the movement of MLC leaves. (Convery and Rosenbloom (1992), Bortfeld et al (1994), Yu, Symons et al (1995); Boyer A. L., and Yu C. X.; (1999);) In contrast, IMAT uses multiple overlapping arcs of radiation in order to produce intensity modulation. (Yu, C. X. (1995); Yu et al (2002))

The complexity of IMRT and IMAT is such that treatment plans cannot be produced through a manual trial and error approach. Instead, one must employ an automated treatment planning system. Furthermore, current automated planning tools are not capable of producing optimized plans for IMAT.

Current inverse-planning algorithms for IMRT use a two-step approach (Boyer and Yu 1999). In the first step, the portal that defines the radiation beam's eye view (BEV) for each radiation beam angle is divided into a set number of finite-sized pencil beams. The radiation dose for each of these pencil beams is then calculated and the corresponding beam intensities are subsequently optimized subject to pre-specified treatment goals. The second step uses the radiation intensity maps from each beam angle and translates the radiation intensity maps into a set of deliverable aperture shapes. During the optimization of the radiation intensity maps, the delivery constraints imposed by the design of various components of the linear accelerator are not taken into account resulting in treatment plans that are often complex and inefficient to deliver.

The two step approach used by current inverse-planning algorithms is unable to generate treatment plans for IMAT. With IMAT, the radiation is delivered while the gantry rotates continuously. Current inverse-planning algorithms fail to take the gantry's continuous movement into account. One feature of IMAT treatment plans is that the aperture shapes for adjacent angles within an arc must not differ significantly. This constraint exists because there are limitations on the speed at which the leaves of the multileaf collimator can travel. This constraint makes it difficult to translate the radiation intensity maps into a set of deliverable arcs.

This invention is an inverse-planning method that does not require the current two-step approach used for IMRT treatment planning. This invention allows for the planning for either IMRT, IMAT, or a new type of intensity-modulated radiotherapy which comprises a combination of IMRT and IMAT. This combination of IMRT and IMAT represents a hybrid approach to IMRT. Hybrid IMRT provides the ability to incorporate into each treatment plan the dosimetric advantages of both IMRT and IMAT. For example, the rotational nature of IMAT can be used to dissipate the deposition of radiation dose to normal tissue while the fixed field capabilities of IMRT allow for a high degree of modulation from any particular beam angle.

It is the purpose of this invention to enable a single planning system to plan for different modes of DART delivery and to simplify the planning and delivery of IMRT. Instead of optimizing the intensity distributions of the beams and then converting them to deliverable MLC field shapes, this invention directly optimizes the shapes and the corresponding weights of the apertures. The combination of these optimally weighted apertures at every beam angle creates highly modulated beam intensity distributions for achieving the clinical objectives of the treatment plan. In the process of optimizing the field shapes, all delivery constraints are considered. For instance, fixed-field delivery would have constraints imposed by the MLC. Rotational delivery would have additional constraints imposed by the speed of the gantry rotation and speed of the MLC leaves.

For fixed-field delivery, the user specifies the number of beams and their angles, the beam energies, and the number of apertures per beam angle. For rotational delivery, the user specifies the number and range of the arcs. The goals of the treatment plan are determined and then quantified with an objective function, which can be of dose-volume based, biological, or of other forms.

For each delivery angle, the maximum extent of the beam aperture is determined based on the beam's eye view of the target with sufficient margins. This beam is then divided into a grid of small beamlets called pencil beams. The dose distribution from each of these pencil beams is calculated using any conventional dose calculation method and stored on an appropriate medium, such as a hard drive. At the start of the optimization, all apertures in the same beam direction are set to the same shape as the maximum extent of the beam. These apertures are then optimized by an optimization algorithm. The optimization process generally involves modifying the shape or weight of the apertures, determining if the modification violates the delivery constraints, and, finally, accepting and rejecting such modifications based on the rules of the optimization. For each modification, a new dose distribution computed based upon the modified aperture shapes or weights. While simulated annealing lends itself well to the optimization method, other optimization techniques could also be used.

The output of the algorithm is a set of deliverable apertures and their weights, which can be transferred to the control system of a linear accelerator and delivered to a patient. Because of the feature of pre-specification of the number of angles and apertures, the user controls the complexity of the treatment plan. Because the invention can incorporate the delivery constraints for each particular linac and MLC, it can be used in conjunction with any commercially available linear accelerator.

DETAILED DESCRIPTION OF THE INVENTION

Figure 4:
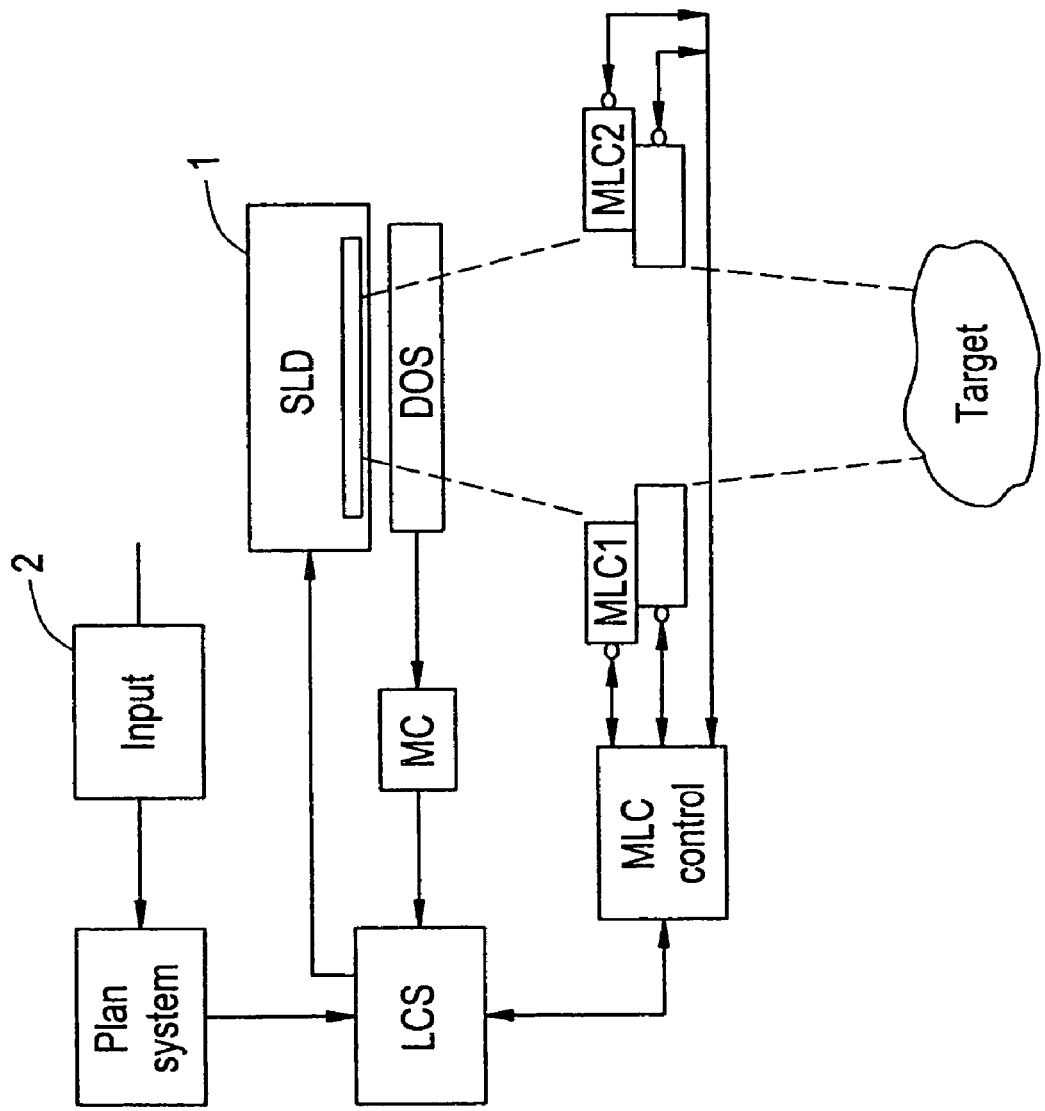
FIG. 4 illustrates an apparatus according to an embodiment of the invention.

Referring to FIG. 4, a linear accelerator (linac) 1 which is a device capable of controlled delivery of radiation to a patient in need of radiation therapy. The radiation exits through the end of the treatment head which is mounted on the gantry (not shown). In some linacs, the treatment head is equipped with a multi-leaf collimator (MLC) which shapes the radiation field. A linac has a control unit in a housing. A linac has a gantry which can rotate about a horizontal axis H of rotation around the patient who is lying on the bed. A linac emits a beam of radiation which is aimed at the patient. The beam of radiation can be photons, electrons, or any other type of radiation used for therapy.

During treatment, the radiation beam is directed on a part of the treatment area on the patient. The gantry can rotate about a horizontal axis of rotation; thus allowing for a change in the angle of treatment.

A MLC has multiple thin leafs which can be made of tungsten alloy or other heavy materials stacked in two opposing banks MLC1, MLC2. For one MLC the leaves are usually identical in width, range of travel, and restrictions in relation to the other leaves in the same bank or opposing banks. MLC leaf restrictions can be characterized as static constraints and dynamic constraints. Static constraints can include, but are not limited to, the maximum distance between the most forward position and the most backward position of any leaf in one bank and the minimum distance between opposing leaves in opposing banks. However, it is understood that different MLC's can have widths ranging from 2 mm to 12 mm, range of travel ranging from 1 cm to over 32 cm, and different restrictions. Dynamic constraints include, but are not limited to, the speed of leaf travel, the acceleration and deceleration. These static and dynamic geometric constraints determine the kind of aperture shapes that a particular MLC can form.

Within a linac and in addition to the MLC, a beam shielding device SLD is provided in the path of radiation beam to supplement the MLC in shaping the radiation fields. The beam shielding device includes a plurality of opposing plates. In one embodiment, additional pairs of plates are arranged perpendicular to the opposing plates. The opposing plates move with respect to the plate axis by a drive unit to change the size of the irradiated field. The drive unit includes an electric motor which is coupled to the opposing plates and which is controlled by a motor controller. Position sensors are also coupled to the opposing plates, respectively for sensing their positions. The plate arrangement may alternatively include a multi-leaf collimator (MLC) having many radiation blocking leaves.

In an MLC, there are opposing banks of leaves. Each opposing leaf is attached to a drive unit. The drive units drive the leaves, in and out of the treatment field, thus creating the desired field shape. The MLC leaves, are relatively narrow, and cast a shadow of about 0.5 cm to 1.0 cm onto the treatment area. The position of the leaves of the MLC defines the aperture shape for a treatment.

The intensity of a beam refers to the amount of radiation that accumulates at a specific location of the treatment portal defined by the linac.

A longer radiation exposure time for a specific location in the treatment portal corresponds to a higher radiation intensity. If the MLC opening is fixed during the entire duration of treatment, all locations in the treatment portal would receive approximately the same amount of radiation, and there would be no intensity modulation. A modulated intensity radiation field occurs when the MLC opening changes such that different locations of the treatment portal are exposed for different durations.

The motor controller is part of the Linac Control System (LCS) that also contains a dosimetry system. The dosimetry system measures the output of the radiation beam with a measuring chamber MC and reports to the Linac Control System (LCS) the amount of radiation being delivered at any given time. The LCS coordinates radiation delivery and MLC leaf movement in order to achieve the desired intensity patterns. The LCS controls execution of the prescription generated by the present invention and transferred to the linac control system from the treatment planning system. During delivery, the MLC leaves move in order to achieve the desired treatment.

During treatment planning, a user is allowed to set the mode of treatment including IMRT or IMAT or a hybrid thereof, and to provide other treatment parameters such as the orientations of beams, ranges of arcs, the number of apertures per beam angle and/or the number of arcs. Using the invention described herein, the planning system automatically optimizes the shape and weightings of the apertures to best meet the objectives of the treatment The end product of the treatment planning process is a treatment plan that meets the dosimetric requirements specified by the physician. Once a treatment plan is approved by the physician, the treatment planning system will generate a prescription, which specifies the proper coordination between radiation delivery and MLC leaf movements. The prescription, therefore, translates the treatment plan into the computer language understood by the Linac Control System (LCS) and programs the linac for the treatment delivery. The prescription of conventional treatments can be entered manually using a keyboard or other input type of device. For IMRT delivery, because of the complexity of the prescription, prescriptions are normally entered via digital media, such as a diskette or CD, or a network link, or any other input type of device. At a given time during the delivery of radiation to a patient, the LCS is receiving information on dose delivery from the dose control unit. The LCS also receives information in real-time from the MLC position sensors. The LCS compares the dose delivery information from both the MLC controller and the dosimetry system controller with the prescription. Depending on the result of the comparison, the LCS may respond in a variety of manners. For example, the LCS may send a signal to the beam triggering system to pause the radiation so that the MLC can advance to the proper location.

The present invention covers the method of planning and delivery of the radiation treatment plan for IMRT, IMAT, and hybrid IMRT. The treatment planning procedure is performed on a treatment planning system which is distinct from the LCS, so that the treatment planning system can generate IMRT treatment plans for all commercially available linacs and MLC's. Prior art IMRT planning inventions can only plan for fixed-field IMRT delivery but not IMAT or hybrid IMRT (U.S. Pat. No. 6,240,161 (Siochi); U.S. Pat. No. 6,260,005 (Yang, et al.)) and there is no distinct separation between the treatment planning system and the LCS.

Direct aperture optimization (DAO) which is described herein optimizes the position of the MLC leaves, thus optimizing the aperture shapes, and optimizes each aperture shape's corresponding intensity based on the treatment goals for a specific patient. With DAO, the geometric constraints of a MLC associated with either IMRT, IMAT, or hybrid IMRT are incorporated during the optimization process, thereby permitting the development of a treatment plan for IMRT, IMAT, and hybrid IMRT in one system. DAO is an improvement over prior arts optimization methods because in the prior art methods each system is dedicated to only gantry-fixed IMRT. Inverse planning for IMAT and hybrid IMRT was not possible with prior arts. Another distinguishing feature of DAO is that all of the geometric constraints imposed by the treatment unit are incorporated into the optimization. Examples of geometric constraints for the MLC and linac include, but are not limited to, the dose rate, gantry speed, and minimal amount of radiation that can be delivered with acceptable accuracy.

Figure 1:
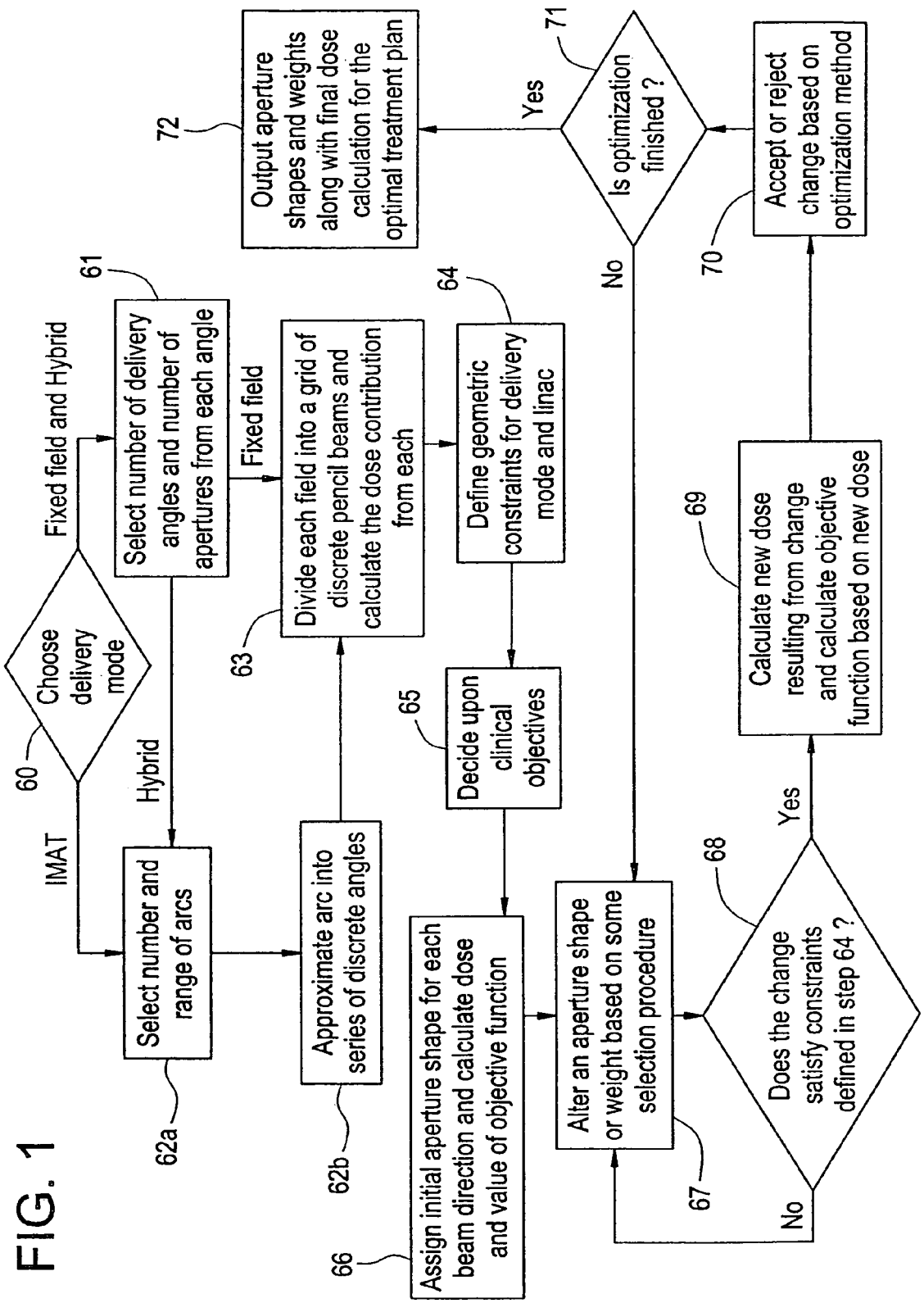
FIG. 1 shows the flow chart for direct aperture optimization.

FIG. 1 shows a flow chart of the DAO procedure. In a first step 60, the mode of delivery is selected. The modes of delivery include IMRT, IMAT, or hybrid IMRT. If fixed field IMRT or hybrid IMRT is selected, in a step 61, the user must select the delivery angles and the number of apertures assigned to each angle. Then one proceeds to step 62a if one selected hybrid IMRT in a step 60. Otherwise, if one selected fixed field IMRT in a step 60, then one proceeds immediately to a step 63. If the user selects IMAT in a step 60, then the user proceeds immediately to step 62a.

In a step 62a, one must select the number of arcs and the range for each arc. After the consideration factors (the delivery angles and number of apertures assigned to each angle for IMRT or the number of arcs and range for each arc for IMAT) are entered, in a step 62b, the treatment planning system automatically calculates evenly spaced radiation beams to approximate the range of rotation of the gantry. Hybrid IMRT required both steps 61 and 62 to account for the combined use of fixed field and arced delivery.

In a step 63, each field is divided into a grid of discrete pencil beams and the dose distribution for each pencil beam is computed. The MLC delivery constraints for fixed field delivery are determined in a step 64. For rotation delivery in a step 64, the constraints associated with rotational delivery are also determined to ensure not only coordination of MLC movement with radiation delivery, but also the synchronization of radiation delivery and gantry rotation.

In a step 65, the user defines the clinical objectives of the treatment plan. These clinical objectives are used to score the quality of the treatment plan throughout the optimization process. The treatment plan quality can be scored by an objective function that reduces the treatment plan into a single numerical value. The objective function can be, by way of example only, a least-square dose difference objective between the desired dose and the achieved dose. The objective function can also be based on dose volume histograms (DVH) or biological based parameters.

The optimization process begins in a step 66, where the treatment planning system assigns an initial aperture shape for each beam angle. In the preferred embodiment, the radiation beam's eye view of the target for each beam angle is used for the starting point, but any aperture shape for each beam angle can be used. The treatment planning system also assigns a relative weight (intensity) to each aperture shape.

In addition, the treatment planning system calculates the radiation dose, the radiation dose distribution, and the dose distribution quality (objective function).

After obtaining an initial score for the dose distribution quality of the plan, the treatment planning system, in a step 67, modifies an optimization variable. The optimization variables that the treatment planning system considers include, but are not limited to, the positions of the MLC leaves used to shape each aperture for each beam angle, and the relative weight (intensity) of each aperture shape assigned to each aperture. A stochastic or deterministic approach can be used to determine the variable for modification and the size of the modification.

Prior to calculating the new dose distribution and objective function resulting from the modification of the optimization variable in a step 67, the treatment planning system determines, in a step 68, if one or more geometric constraints is violated by the modification. Examples of geometric constraints include, but are not limited to, the MLC leaf positions for the particular linear accelerator, the linac gantry speed, the dose rate, and MLC leaf travel speed. If the proposed modified aperture shape or intensity violates any of geometric constraints, the treatment planning system rejects the modified aperture shape and returns to a step 67.

If none of the geometric constraints is violated in a step 68, then the treatment planning system calculates the radiation dose applied to the treatment area as a result of the modification. The value of the objective function is calculated from the new radiation dose, and the dose distribution quality is compared to the dose distribution quality prior to the modification. If the value of the objective function changed in the desired direction, the treatment planning system accepts the proposed modification of the aperture shape. If the radiation dose and dose distribution quality are not within acceptable ranges or the objective function changes in the undesirable direction, the treatment planning system either accept or rejects the proposed modification of the aperture shapes based on a series of pre-set rules and returns to a step 67.

In the preferred embodiment of this invention, a simulated annealing algorithm is used in steps 67 through 70 to determine the optimal aperture shapes and corresponding weights. The optimization algorithm randomly selects a variable from the set of variables considered in the optimization process, i.e., the MLC leaf positions and the weights of the aperture shape. For the selected variable, a change of random size is sampled from a probability distribution. For instance, a Gaussian distribution could be used. In addition, the shape of the curve could change with successive iteration of the procedure. For instance, the width of the Gaussian plot could decrease according to some schedule such as in Formula (1):

$$\sigma = 1 + (A-1)e$$

where A is the initial Gaussian width, ns , , , is the number of successful iterations, and TstePo quantifies the rate of cooling. Although the above schedule is specific, any schedule can be used. For instance, the step size could be constant throughout the optimization. The goal of this invention is to achieve the optimal aperture shape for each beam angle as quickly as possible. Decreasing the amplitude of change as the optimization progresses allows coarse samples in the beginning and fine-tuning at the end of the optimization process.

Other types of optimization algorithms can be used in this invention such as conjugate gradient or genetic algorithms.

Based on pre-defined termination criteria which are dictated by the optimization algorithm, the treatment planning system will cease the optimization process in step 71. The plan with the optimal value of the objective function is deemed the optimal plan. This optimum treatment plan is a set of deliverable aperture shapes and the intensities associated with each aperture shape. Monitor units are units of radiation output from a linac.

In a step 72, the treatment planning system provides the optimum treatment plan and final radiation dose distribution to a user for review by displaying the optimum treatment plan on a display screen, or printing it out using a printer, or placing it on some other user interface which is known in the art field.

In an optional step 73, the final radiation dose distribution resulting from the optimum treatment plan is optionally reviewed and approved by a user capable for reviewing such information.

In a step 74, after optional review and approval, the optimum treatment plan is transferred from the treatment planning system performing the direct aperture optimization to the LCS in the form of a Prescription file. The optimal treatment plan is loaded onto the LCS via a diskette, a computer network link, or any other means known in the art field capable of transferring data between two distinct computers. This invention allows the direct aperture optimization information a to be transmitted from the treatment planning system located at one site to the linac control system (LCS) located at a different site.

Because the treatment planning system is distinct from the linac control system (LCS), one can optimize several different treatment plans for different types of linear accelerators in succession or concurrently.

Figure 2:
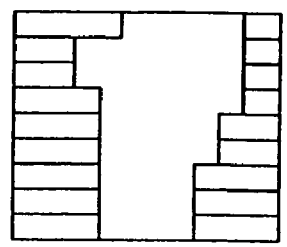
FIG. 2 illustrates three aperture shapes determined using direct aperture optimization.
Figure 2:
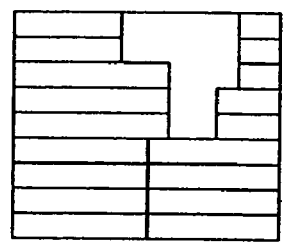
Figure 2:
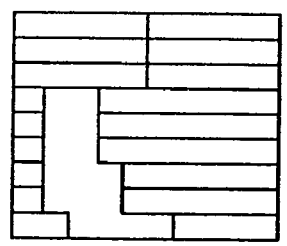

FIG. 2 illustrates three aperture shapes obtained by using the DAO of this invention assigned to a radiation beam direction. As compared with the aperture shapes obtained from a typical leaf sequencing step using the prior art treatment planning programs, the exposed area of each aperture shape is significantly increased, resulting in greater efficiency in delivery.

Figure 3:
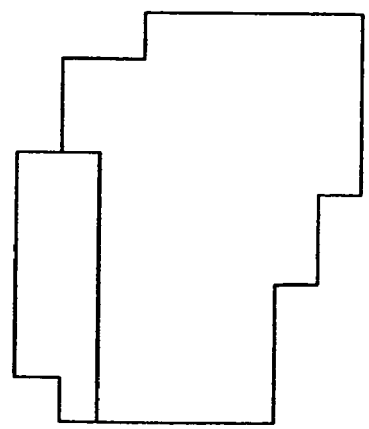
FIG. 3 illustrates the intensity map for three aperture shapes determined using directaperture optimization.

FIG. 3 illustrates the intensity distribution created with the three apertures shown in FIG. 2. Theoretically, the number of intensity levels, N, resulting from n apertures can be expressed as: $N = --2° -1$. For example, with three aperture shapes per beam, seven intensity levels can be created. Moreover, because each intensity level is a free-floating percentage of the maximum intensity as compared to fixed percentage of the maximum intensity in the previous arts of IMRT planning, the seven intensity levels created by overlapping directly optimized apertures give more flexibility to the planning system in creating optimal treatment plans. In the prior art IMRT treatment planning, an intensity pattern containing 7 intensity levels would require 15 to 30 apertures to realize, resulting in very inefficient treatment delivery. Moreover, when such large number of apertures is used, the aperture shapes are generally small, requiring very high accuracy in the positions of the MLC leaves. As the result, quality assurance efforts must be intensified to levels much beyond conventional treatments. With the invention described herein, the benefit of IMRT can be realized without such inefficiency and labor intensiveness associated with IMRT using prior arts.

REFERENCES

1. Bortfeld, T. R.; Kahler, D. L.; Waldron, T. J.; and Boyer, A. L.; "X-ray Field Compensation With Multileaf Collimators"; Mt. J. Rad. Oncol. Biol. Phys., 28(3): 723-730 (1994).
2. Levitt, S. H.; Khan, F. M.; Potish, R. A.; and Perez, C. A.; "Technological Basis of Radiation Therapy—Clinical Applications." Third Edition, published by Lippincott William & Wilkins (1999).
3. Convery, D. J.; and Rosenbloom, M. E.; "The Generation of Intensity-Modulated" Phys. Med. Biol., 37(6): 1359-1374 Fields for Conformal Radiotherapy by Dynamic Collimation; (1992).
4. Boyer, A. L.; and Yu, C. X.; "Intensity-Modulated Radiation Therapy with Dynamic Multileaf Collimators", Seminars in Radiation Oncol., 9(1): 48-59 (1999).
5. Yu, C. X.; Symons, M. J.; Du, M. N.; et al.; "A Method for Implementing Dynamic Photon Beam Intensity Modulation Using Independent Jaws and Multileaf Collimator"; Phys. Med. Biol., 40: 769-787 (1995).
6. U.S. Pat. No. 6,240,161 (Siochi);
7. U.S. Pat. No. 6,260,005 (Yang, et al.),
8. Webb S.; The Physics of Conformal Radiotherapy (Institute of Physics Publishing, Bristol, 1997).
9. Yu, C. X.; "Intensity-Modulated Arc Therapy With Dynamic Multileaf Collimation: An Alternative to Tomotherapy"; Phys. Med. Biol.; 40: 1435-49 (1995).
10. Yu C. X, Li XA, Ma L, Shepard D, Holmes T, Sarfaraz M, Suntharalingam M, Mansfield CM: Clinical implementation of intensity modulated arc therapy. Int. J. Rad. Oncol. Biol. Phys., 53(2) 453-463, 2002.

While the disclosure above describes the invention in detail and with reference to specific embodiments thereof, it will be apparent to one of ordinary skill in the art that various changes and modifications can be made therein without departing from the spirit and scope thereof.

What is claimed is:

1. A method for planning a radiation treatment of a target area comprising:
    selecting at least one of a set of parameters a) and b), wherein a) includes a number of delivery angles for a radiation beam for performing radiation treatment and a number of apertures through which the radiation beam is directed towards the target area and wherein b) includes a number and range of arcs through which the radiation beam travels;
    assigning an initial aperture configuration for the radiation beam prior to determining any intensity distribution for any radiation beam to treat the target area;
    calculating an initial radiation dose distribution to a target area of a patient based on the initial aperture configuration; and
    applying the initial radiation dose distribution to determine a final radiation dose distribution to be applied to the target area.

2. The method of claim 1, wherein selecting at least one of the set of parameters a) and b) comprises selection of at least one of the set of parameters a) and b) by an operator.

3. The method of claim 1, wherein the final radiation dose distribution comprises a dose distribution that satisfies an objective function, and wherein the final radiation dose distribution to the patient is directly applied to the patient without further calculation of radiation dose.

4. The method of claim 3, wherein the final radiation dose distribution is determined iteratively from the initial dose distribution through altered radiation dose distributions.

* * * * *